United States Patent [19]

Peet et al.

[11] Patent Number: 5,661,167
[45] Date of Patent: Aug. 26, 1997

[54] PROLYL ENDOPEPTIDASE INHIBITORS

[75] Inventors: Norton P. Peet; Shujaath Mehdi, both of Cincinnati; Joseph P. Burkhart, West Chester, all of Ohio

[73] Assignee: Merrell Pharmaceuticals Inc., Cincinnati, Ohio

[21] Appl. No.: 759,323

[22] Filed: Dec. 2, 1996

Related U.S. Application Data

[63] Continuation of Ser. No. 503,216, Jul. 17, 1995, abandoned, which is a continuation of Ser. No. 161,106, Dec. 2, 1993, abandoned.

[51] Int. Cl.$^6$ ...................... A61K 31/425; C07D 417/14
[52] U.S. Cl. ..................... 514/365; 548/200; 548/518
[58] Field of Search ............... 548/200; 514/365

[56] References Cited

U.S. PATENT DOCUMENTS

| | | |
|---|---|---|
| 4,518,528 | 5/1985 | Rasnick et al. . |
| 4,855,303 | 8/1989 | Hoover et al. . |
| 4,912,127 | 3/1990 | Henning ................................ 514/422 |

FOREIGN PATENT DOCUMENTS

| | | |
|---|---|---|
| 0195212 | 9/1986 | European Pat. Off. . |
| 0286928A2 | 4/1988 | European Pat. Off. . |
| 0414903A1 | 12/1989 | European Pat. Off. . |
| 0419683A1 | 4/1990 | European Pat. Off. . |

OTHER PUBLICATIONS

Yoshimoto, et al., Agric. Biol. Chem. 55(1), 37–43, 1991.
Saito, et al., J. Enzyme Inhibition, 1991, vol. 5, pp. 51–75.
CA Selects: Amino Acids, Peptides, & Proteins, Issue 16, 1991, 115:50303q abstracting Uchida, et al., PCT Int. Appl. WO 90 12,005 18 Oct. 1990.
CA Selects: Amino Acids, Peptides, & Proteins, Issue 9, 1991, 114: 164802m abstracting Shioiri, et al., EP Appl. 384,341, 29 Aug. 1990.
Atack, et al., European Journal of Pharmacology, 205 (1991) 157–163.
Wilk, et al., Journal of Neurochemistry, vol. 41, No. 1, 69–75, 1983.
Friedman, et al., Journal of Neurochemistry, vol. 42, No. 1, 237–241, 1984.
Nishikata, et al., Chem. Pharm. Bull. 34(7) 2931–2936 (1986).
Yoshimoto, et al., Agric. Biol. Chem., 55(1), 37–43, 1991.
CA Selects: Amino Acids, Peptides, & Proteins, Issue 24, 1991, 115:232893q abstracting Furukawa, et al., JP 03 56,460, 12 Mar. 1991.
CA Selects: Amino Acids, Peptides, & Proteins, Issue 24, 1991, 115:232874j abstracting Furukawa, et al., JP 03 56,461, 12 Mar. 1991.
Bakker, et al., Bioorganic & Medicinal Chemistry Letters, vol. 1, No. 11, pp. 585–590, 1991.
Tsuru, et al., J. Biochem. 104, 580–586 (1988). J. Burkhart to KJC Mar. 20, 1992.
Yoshimoto, et al., Biochemistry, vol. 16, No. 13, pp. 2942–2948, 1977.
Angelastro, et al., Tetrahedron Letters, vol. 33, No. 23, pp. 3265–3268, 1992.
Sham, H.L. et al., FEBS Letters, vol. 220, No. 2, pp. 299–301 (1989).
Powers, J.C., Eleventh American Peptide Symposium, Abstracts, The Salk Institute and University of CA, San Diego (1989).
Imperiali, B., et al., Biochemistry, vol. 25, 3760–3767 (1986).
Stein, R.L., et al., Biochemistry 26, 2682–2689 (1987).
Chemical Abstracts 110:76058k, vol. 110 (1989), abstracting Angliker, H., et al., Biochem. J. 256(2), 481–6, 1988.
Chemical Abstracts 106:850589f, vol.106 (1987), abstracting JP 86, 183,253, Aug. 15, 1986.
Ueda, T. et al., Biochem. J. 265, 539–545 (1990).
Synthesis, 676–678 (1983). Internal report.
Gassman, P.G., et al., J. Org. Chem. 52, 2481–2490 (1987). Internal report.
Tsuru, et al., J. Biochem., 104, 580–586 (1988).

*Primary Examiner*—Robert Gerstl
*Attorney, Agent, or Firm*—Kenneth J. Collier

[57] ABSTRACT

The present invention relates to compounds of formula 1,

Formula 1

$$A\text{-}OCO\text{-}N\underset{}{\overset{X_1}{\diagup\diagdown}}CO\text{-}N\underset{CCF_2B}{\overset{X_2}{\diagup\diagdown}}\overset{O}{\|}$$

including all of its stereoisomers, compositions, and processes for preparation of the same. The compounds of the present invention are also useful in their pharmacological activities as they directly act as inhibitors of prolyl endopeptidase and thereby provide a methods for memory enhancement, preventing or slowing the affects of amnesia or memory deficits.

6 Claims, No Drawings

PROLYL ENDOPEPTIDASE INHIBITORS

CROSS-REFERENCE TO RELATED APPLICATION

This is a continuation of application Ser. No. 08/503,216, filed Jul. 17, 1995; abandoned which is a continuation of application Ser. No. 08/161,106 filed Dec. 2, 1993 abandoned which is herein incorporated by reference.

Peptide bonds linked to proline appear to be relatively resistant to the broad-specificity peptidases (Mentlein, 1988), suggesting that peptidases that hydrolyze peptide bonds containing proline may be important in the metabolism of proline-containing peptides (Atack, et al., Eur. J. of Pharm., 205, 157–163 (1991). Prolyl endopeptidase appears to play such a role in the metabolism of biologically active proline containing peptides. The enzyme hydrolyzes many biologically active peptides containing proline, such as oxytocin, thyrotropin releasing hormone, luteinizing hormone releasing hormone, angiotensin II, bradykinin, substance P, neurotensin and vasopressin.

Prolyl endopeptidase acts to degrade active peptides as a carboxy terminal proline cleaving enzyme. Specifically, prolyl endopeptidase acts by hydrolyzing peptide bonds on the carboxy side of proline residues. Prolyl endopeptidase is thought mechanistically to act as a serine protease, cleaving peptide bonds by a mechanism similar to other serine proteases such as α-chymotrypsin, trypsin, and subtilisins.

Although the enzyme universally acts at peptide bonds containing proline derivatives, the enzyme form appears to vary in different tissue sources, wherein the enzyme shows differences in substrate specificity. Prolyl endopeptidase has been purified from a number of plant (carrots, mushrooms), microbial (*Flavobacterium menigosepticum*) and animal tissues. In animals, the enzyme is found ubiquitously throughout the body, however, prolyl endopeptidase is generally found in highest concentrations within the CNS (Wilk, 1983). Common sources of the enzyme for testing substrates against animal sources have been bovine, rat, and mouse brain.

Low molecular weight inhibitors of prolyl endopeptidase have been studied. These inhibitors are generally chemical derivatives of proline or small peptides containing terminal prolines. Benzyloxycarbonyl-prolyl-prolinal has been shown to be a specific transition state inhibitor of the enzyme (Wilk, S. and Orloeski, M., J. Neurochem., 41, 69 (1983), Friedman, et al., Neurochem., 42, 237 (1984)). N-terminal substitutions of L-proline or L-prolyl-pyrolidine (Atack, et al., Eur. J. of Pharm., 205, 157–163 (1991), JP 03 56,460, EP 384,341), as well as variations of N-benzyloxycarbonyl (Z) dipeptides containing prolinal at the carboxy terminus have been synthesized as prolyl endopeptidase inhibitors (Nishikata, et al., Chem. Pharm. Bull. 34(7), 2931–2936 (1986), Baker, A. et al., Bioorganic & Medicinal Chem. Letts., 1(11), 585–590 (1991)). Thioproline, thiazolidine, and oxopyrrolidine substitutions of the core structure have been reported to inhibit prolyl endopeptidase (Tsuru, et al., J. Biochem., 94, 1179 (1988), Tsuru, et al., J. Biochem., 104, 580–586 (1988), Saito et al., J. Enz. Inhib. 5, 51–75 (1991), Uchida, I., et al. PCT Int Appl. WO 90 12,005, JP 03 56,461, JP 03 56,462). Similarly, various modifications of the carboxy terminal proline have been made, including various fluorinated ketone derivatives (Henning, EP 4,912,127). General syntheses of fluorinated ketone derivatives has been described (Angelastro, M. R., et al., Tetrahedron Letters 33(23), 3265–3268 (1992). Other compounds such as chloromethyl ketone derivatives of acyl-proline or acyl-peptide-proline (Z-Gly-Pro-$CH_2Cl$) have been demonstrated to inhibit the enzyme by alkylating the enzyme's active site (Yoshimoto, T., et al., Biochemistry 16, 2942 (1977).

SUMMARY OF THE INVENTION

The present invention claims peptide derivatives of formula 1, including all of its stereoisomers:

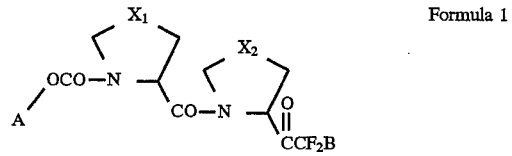

Formula 1 wherein;

A is benzyl or a t-butyl group;

$X_1$ is —S— or —$CH_2$—; and $X_2$ is —S— or —$CH_2$—;

B is —$CF_3$ or —$CF_2CF_3$.

It is understood that preferred derivatives of formula I are contained within the markush groupings and therefore further groupings may be elected to form subgroupings containing those elected substitutents. Preferred groupings of formula I may also be elected to further include the embodiments of the demonstrated examples shown herein.

The compounds of formula 1 are important inhibitors of the enzyme prolyl endopeptidase. The novel inhibitors are diprolyl peptide derivatives containing carboxy terminal pentafluoroethyl substituents. In the diprolyl peptide derivatives, the proline moiety may optionally be substituted with thioproline derivatives, as when $X_1$ or $X_2$ are chosen to be sulfur. The peptide analogs of this invention potentially possess significant inhibitory activity of prolyl endopeptidase, and therefore, may allow for a scientifically interesting and therapeutically significant adjunct to the treatment of amensia and memory deficits as well as to enhance memory function. Moreover, the presence of thiazolidine functionalities may provide for enhanced potency and extended duration of action for these compounds.

A further object of the present invention is the inhibition of the proteolytic activity of prolyl endopeptidase as a model for therapeutic intervention for memory restoration or enhancement. Inhibition of the proteolytic activity may serve to control undesirable high levels of the enzyme. Inhibitors of prolyl endopeptidases have been reported to have antiamnesic effects in rat and mouse models by a number of groups (See Yoshimoto, et al., J. Pharmacobio-Dyn., 10, 730 (1983) and Saito et al., J. Enz. Inhib. 3, 163 (1990), Uchida, I., et al. PCT Int Appl. WO 90 12,005). While not wishing to be bound by theory, it is believed that the correlation of enhanced memory with prolyl endopetidase inhibition is due to the ability of the enzyme to degrade vasopressin. Further, inhibitors of prolyl endopeptidase have been shown to reverse the effects of scopolamine-induced memory deficits in mice (Atack, et al., Eur. J. of Pharm., 205, 157–163 (1991).

The synthetic preparation of the dipeptides of present invention are shown in Scheme I and then are described on the following pages.

SYNTHESIS OF PROLYL ENDOPEPTIDASE INHIBITORS

Scheme I, parts A through G, shows synthesis of compounds of formula 1.

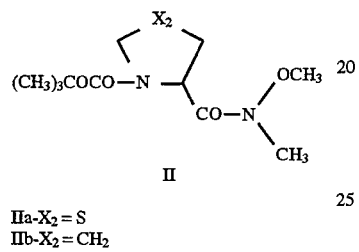
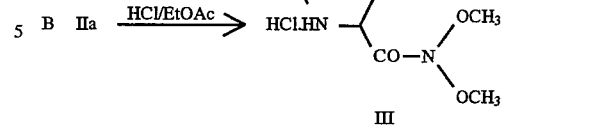
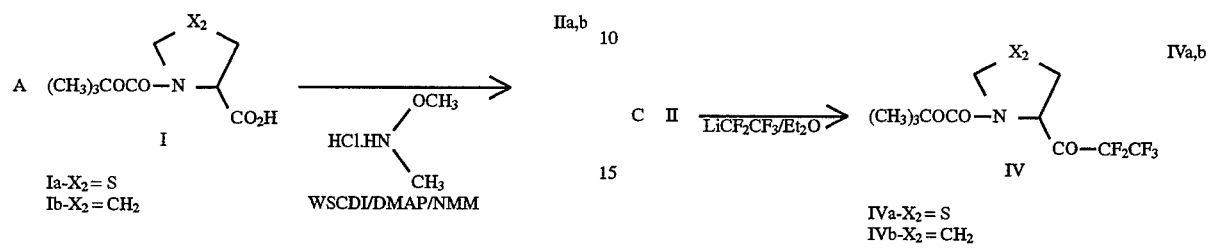

Essential intermediates for the synthesis of compounds of formula 1 having carboxy terminal pentafluoroethyl ketones (compounds IVa and IVb) or methoxymethylamino amides (compounds IIa and IIb) can be essentially prepared by the methods described by Angelastro, M., (Tetrahedron Letters,

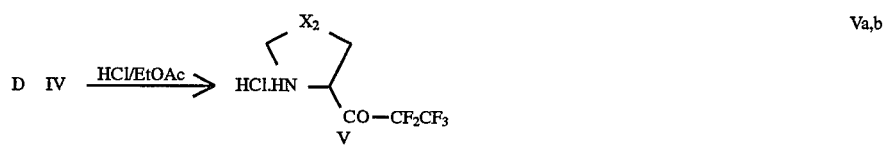
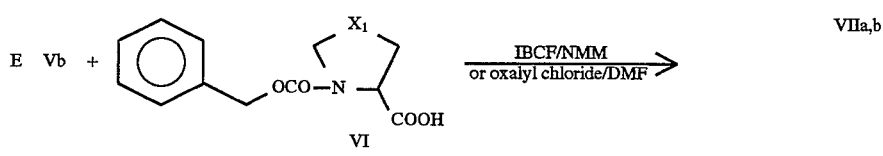
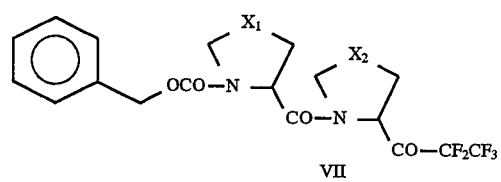
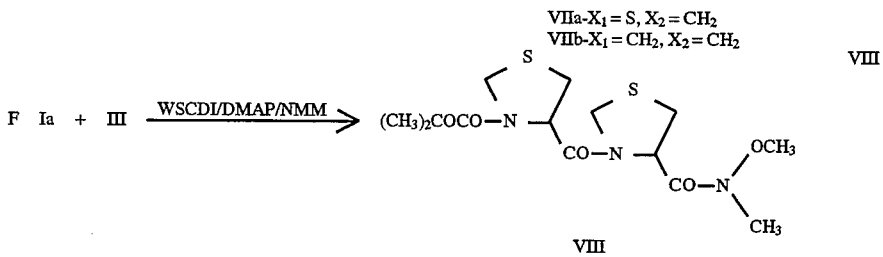

33(23), 3265–3268 (1992) and Nahm, S. and Weinreb, S. M., Tetrahedron Letters, 22, 3815 (1981).

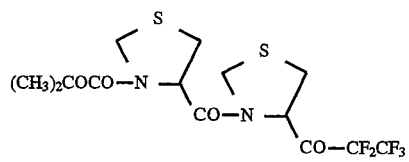

Scheme I, step A, shows the general preparation of methoxymethylamino amides of formula IIa and IIb. Compounds of formula IIa and IIb may be prepared from t-butoxycarbonyl protected proline (2-pyrrolidinecarboxylic acid, 1,1-dimethylethyl ester) and thioproline (thiazolidine-3,4-dicarboxylic acid, 1,1-dimethylethyl ester) derivatives by reaction with N,O-dimethylhydroxylamine hydrochloride. This reaction can be performed essentially as described by Nahm, S. and Weinreb, S. M., Tetrahedron Letters, 22, 3815 (1981). Essentially the coupling of N,O-dimethylhydroxylamine hydrochloride can be done by using a suitable coupling reagent such as a water soluble carbodiimide, or the like, and the product can be purified by standard means of isolation known in the art.

Step B shows that the t-butoxycarbonyl protecting group of the thioprolines of IIa can be removed by suitable acid treatment, such as by hydrochloric acid treatment in ethyl acetate, to produce the corresponding N-methoxy-N-methyl-4-thiazolidinecarboxamide, monohydrochloride (compound III). The final product can then be suitably purified using conventional isolation techniques known to those in the art.

Through Step C, the compounds of II can be converted into the pentafluoroethyl ketones of IVa and IVb. Reaction with pentafluorethyllithium generated in situ from pentafluoroethyl iodide and methyllithium.lithium bromide complex is a suitable means of conversion of the hydroxamates of compound IIa or IIb to compounds of formulas IVa or IVb, respectively. This reaction is performed essentially as described by Angelastro, M. R., et al. Tetrahedron Letters, 33, 3265 (1992). The final product can be suitably purified using conventional isolation techniques known to those in the art.

Step D shows that the t-butoxycarbonyl protecting group of IVa or IVb is acid liable and can be removed by suitable acid treatment, such as by hydrochloric acid treatment in ethyl acetate. Treatment with acid produces the corresponding compounds of formulas Va or Vb (4-(2,2,3,3,3-pentafluoro-1-oxopropyl)-thiazolidine, monohydrochloride or 2-(2,2,3,3,3-pentafluoro-1-oxypropyl)pyrrolidine, hydrochloride, respectively). The final product can be suitably purified using conventional techniques known to those in the art.

Step E generally shows the condensation of two suitably protected amino acids to form either the 2-[[2-(2,2,3,3,3-pentafluoro-1-oxopropyl)-1-pyrrolidinyl]carbonyl]-1-pyrrolidinecarboxylic acid, phenylmethyl ester (VIIb) or 4-[[2-(2,2,3,3,3-pentafluoro-1-oxopropyl)-1-pyrrolidinyl]carbonyl]-3-thiazolidinecarboxylic acid, phenylmethyl ester (VIIa) or the like. Condensation of the two protected amino acids to form an amide linkage between the two pieces is well-known in the art. Several methods of condensation are known including, as shown, conversion of the carboxy terminal acid of compound IV with oxalyl chloride in a suitable solvent, such as dimethyformamide. The acid chloride can then be condensed with the alpha-amino group of Vb. The final product can then be purified using conventional techniques known to those in the art.

Step F shows the preparation of the dithiazolidine derivatives of compound VIII, like the 4-[[4-[(methoxymethylamino)carbonyl]-3-thiazolidinyl]carbonyl]-3-thiazolidinecarboxylic acid, 1,1-dimethylethyl ester. Condensation of compounds such as Ia with III with a coupling reagent to form an amide linkage between the two protected amino acids is well known in the art. Several methods of condensation are known including, condensations carried out with various carbodiimides, such as, water soluble carbodiimide. Following condensation, the final product can then be purified using conventional techniques known to those in the art.

As in Step C, dipeptides having a terminal methoxymethylaminocarbonyl are subject to substitution as shown in Step G. Compound VIII can undergo substitution with perfluoroethyl lithium, generated in situ (See Step C), to form the corresponding 4-[[4-(2,2,3,3,3-pentafluoro-1-oxopropyl)-3-thiazolidinyl]carbonyl]-3-thiazolidinecarboxylic acid, 1,1-dimethylethyl ester. Following substitution the final product can be purified using conventional isolation techniques known to those in the art.

Naturally occurring proline derivatives contain a chiral carbon atom. Specifically it is realized that the carbon alpha to the nitrogen of the ring of both proline and thioproline are chiral. Therefore, the proline and thiazoproline derivatives may exist as one or more of the possible stereoisomers. Unless otherwise specifically indicated, the optically active amino acids, referred to herein, are of the L-configuration. However, chirality can be specifically designated to be either of the D- or L-configuration.

It is understood that the ketone functionality can exist as the ketone or as the hydrated ketone or a mixture of the two states. For instance, the pentafluoroethyl ketone group may be named as 2,2,3,3,3-pentafluoro-1,1-dihydroxypropyl) or 2,2,3,3,3-pentafluoro-1-oxopropyl substituents.

The α-amino protecting group employed with each amino acid introduced into the polypeptide sequence may be any such protecting group known to the art. Among the classes of α-amino protecting groups contemplated are (1) acyl type protecting groups such as: formyl, trifluoroacetyl, phthalyl, toluenesulfonyl (tosyl), benzenesulfonyl, nitrophenylsulfenyl, tritylsulfenyl, o-nitrophenoxyacetyl and α-chlorobutyryl; (2) aromatic urethane type protecting groups such as benzyloxycarbonyl and substituted benzyloxycarbonyl, such as p-chlorobenzyloxycarbonyl, p-nitrobenzyloxycarbonyl, p-bromobenzyloxycarbonyl, p-methoxybenzyloxycarbonyl, 1-(p-biphenylyl)-1-methylethoxycarbonyl, α-dimethyl-3,5-dimethoxybenzyloxycarbonyl and benzhydryloxycarbonyl; (3) aliphatic urethane protecting groups such as tert-butyloxycarbonyl (Boc), diisopropylmethoxycarbonyl, isopropyloxycarbonyl, ethoxycarbonyl and allyloxycarbonyl; (4) cycloalkyl urethane type protecting groups such as cyclopentyloxycarbonyl, adamantyloxycarbonyl and cyclohexyloxycarbonyl; (5) thiourethane type protecting groups such as phenylthiocarbonyl; (6) alkyl type protecting groups such as triphenylmethyl (trityl) and benzyl; and (7) trialkylsilane groups such as trimethylsilane. The preferred α-amino protecting groups are tert-butyloxycarbonyl (Boc) or benzyloxycarbonyl.

The uses of compounds of formula 1 as therapeutics and their mode of administration are described on the following pages.

Therapeutic Use

Use of the compound of the invention as a memory enhancing agent includes improved mental capacity, ability to recall cognitive events, and learned motor activities. As such the compounds of the present invention may be useful in patents suffering from aphasia, apraxia, agnosia, or any type of amnesias, including retrograde and post-traumatic amnesia, benign forgetfulness, and Korsakoff's syndrome (Merck Manual of Diagnosis and Therapy, 15th Addition (1987). Because the compounds are potentially useful in the treatment of memory enhancement and function they may additionally be useful in preventing or slowing memory deficits.

Therapeutic Administration

The appropriate dose of a peptide derivative of this invention when used in the treatment of a patient in need thereof is from 0.2 mg/kg to 250 mg/kg of patient body weight per day depending on other factors involving the particular patient and the peptide derivative selected. The suitable dose for a particular patient can be readily determined. Preferably from 1 to 4 daily doses would be administered typically with from 5 mg to 100 mg of active compound per dose. The amount of a peptide of this invention required can be readily determined by those Skilled in the art.

The term "patient" used herein is taken to mean mammals such as primates, including humans, sheep, horses, cattle, pigs, dogs, cats, rats and mice.

Although some of the peptide derivatives may survive passage through the gut following oral administration, applicants prefer non-oral administration, for example, subcutaneous, intravenous, intramuscular or intraperitoneal; administration by depot injection; by implant preparation; or by application to the mucous membranes, such as, that of the nose, throat and bronchial tubes, for example, in an aerosol can containing a peptide derivative of this invention in a spray or dry powder form.

For parenteral administration the compounds may be administered as injectable dosages of a solution or suspension of the compound in a physiologically acceptable diluent with a pharmaceutical carrier which can be a sterile liquid such as water and oils with or without the addition of a surfactant and other pharmaceutically acceptable adjuvants. Illustrative of oils which can be employed in these preparations are those of petroleum, animal, vegetable, or synthetic origin, for example, peanut oil, soybean oil, and mineral oil. In general, water, saline, aqueous dextrose and related sugar solutions, ethanol and glycols such as propylene glycol or polyethylene glycol are preferred liquid carriers, particularly for injectable solutions.

As pharmacologically useful agents, compounds of formula 1 can be administered in various manners to the patient being treated to achieve the desired effects, such that, the compounds can be administered either alone or in combination with a pharmaceutically acceptable carrier.

As used herein, the following abbreviations are used in describing examples of compounds or uses of the present invention.

| ABBREVIATIONS | |
|---|---|
| Boc-L-Pro-OH | N-tert-butoxycarbonyl-L-proline |
| CBZ-L-Pro-OH | N-carbobenzoxy-L-proline |
| CBZ-L-Pro-Cl | N-carbobenzoxy-L-prolyl chloride |
| CBZ-L-ThioPro-OH | N-carbobenzoxy-L-thioproline |
| CBZ-Gly-Pro-p-nitroanilide | N-carbobenzoxy-glycinyl-L-proline-p-nitroanilide |
| cm | centimeter |
| DMAP | 4-dimethylaminopyridine |
| DMSO | dimetylsulfoxide |

| ABBREVIATIONS -continued | |
|---|---|
| DTT | dithiothreitol |
| EDTA | ethylenediaminetetraacetic acid |
| HEPES | 4-(2-hydroxyethyl)-1-piperazine-ethanesulfonic acid |
| [I] | concentration of inhibitor |
| $K_i$ | inhibition constant |
| KOH | potassium hydroxide |
| NMM | N-methylmorpholine |
| $^1$H-NMR | hydrogen-1 nuclear magnetic resonance |
| $^{19}$F-NMR | flourine-19 nuclear magnetic resonance |
| M | molar |
| MH+ | protonated parent ion mass |
| ml | milliliter |
| min | minute |
| mol | mole |
| mmol | millimole |
| nm | nanometers |
| pH | negative log of the hydrogen ion concentration |
| [S] | substrate concentration |
| TLC | thin-layer chromatograhy |
| WSCDI | water soluble carbodiimide, specifically 1-(3-dimethylaminopropyl)-3-ethylcarbodiimide hydrochloride |
| $v_o$ | initial kinetic rate |

EXAMPLES

The invention will be further clarified by a consideration of the following examples, which are intended to be purely exemplary of the use of the invention. Other embodiments of the invention will be apparent to the skilled in the art from a consideration of this specification or practice of the invention disclosed herein. This invention is illustrated by the following, nonlimiting examples given in the Table 1 below and as further described herein.

TABLE 1

| Compounds | Example/ MDL No. | Emperical Formula | Scheme I Structure |
|---|---|---|---|
| 2-[[2-(2,2,3,3,3-pentafluoro-1-oxopropyl)-1-pyrrolidinyl]carbonyl]-1-pyrrolidinecarboxylic acid, phenylmethyl ester | EXAMPLE I 100,527-01 | $C_{20}H_{21}F_5N_2O_4$ | VIIb |
| 4-[[2-(2,2,3,3,3-pentafluoro-1-oxopropyl)-1-pyrrolidinyl]carbonyl]-3-thiazolidinecarboxylic acid, phenylmethyl ester | EXAMPLE II 102,916-01 | $C_{19}H_{19}F_5N_2O_4S$ | VIIa |
| 4-[[4-(2,2,3,3,3-pentafluoro-1-oxopropyl)-3-thiazolidinyl]carbonyl-3-thiazolidinecarboxylic acid, 1,1-dimethylethyl ester | EXAMPLE IV 100,676-01 | $C_{15}H_{20}F_5N_2O_4S_2$ | IX |

Example 1

I. Synthesis of 2-[[2-(2,2,3,3,3-pentafluoro-1-oxopropyl)-1-pyrrolidinyl]carbonyl]-1-pyrrolidinecarboxylic acid, phenylmethyl ester (Scheme I, compound VIIb)

IA. Synthesis of (R)-2-[(methoxymethylamino)carbonyl] -1-pyrrolidinecarboxylic acid, 1,1-dimethylethyl ester (Scheme I, compound IIb)

To a stirred solution of Boc-L-Pro-OH (4.31 g; 20.0 mmol) and DMAP (2.44 g; 20.0 mmol) in methylene chloride (125 ml) under argon was added N,O-dimethylhydroxylamine hydrochloride (1.95 g; 20.0 mmol) and NMM (2.20 ml; 20.0 mmol). Water soluble carbodiimide (3.83 g; 20.0 mmmol) was then added to the solution. The reaction was allowed to proceed overnight before concentrating to about 20 ml. The concentrated suspension was purified by flash chromatography by loading the suspension onto a 8×14 cm silica gel column and eluting with ethyl acetate/hexane (60:40). Fractions containing the entitled product (Rf=0.32) were combined and concentrated to give a colorless oil (3.21 g). Mass spectrum analysis of the product gave MH+=259.1655 [expected mass for $C_{12}H_{23}N_2O_4$=259.1658].

IB. Synthesis of 2-(2-(2,2,3,3,3-pentafluoro-1-oxopropyl)-1-pyrrolidinecarboxylic acid, 1,1-dimethylethyl ester (Scheme I, compound IVb)

To a stirred solution of 2-[(methoxymethylamino)carbonyl]-1-pyrrolidinecarboxylic acid, 1,1-dimethylethyl ester (compound from Example IA; 1.03 g; 4.00 mmol) in ethyl ether (35 ml) under argon at −78° C. was added perfluoroethyl iodide (1.5 ml; 12.8 mmol) followed by methyl lithium.lithium bromide (1.5M in ethyl ether; 7.5 ml; 11.25 mmol). After thirty minutes at −78° C., the solution was allowed to warm to 0° C. in an ice-water bath. The reaction was quenched by the addition of $KHSO_4$ (1.36 g; 10.0 mmol) in $H_2O$ (8 ml). After several minutes of vigorous stirring both layers of the biphasic suspension became clear and the mixture was transferred to a separatory funnel containing $H_2O$ (50 ml). The layers were separated and the organic phase was washed with a half saturated aqueous solution of $NaHCO_3$ (50 ml) followed by brine (25 ml). The organic phase was dried over magnesium sulfate and concentrated to give a pale yellow oil (1.3 g).

The product was purified by flash chromatography on a 5×15 cm silica gel column eluting with 1.3 liters of ethyl acetate/hexane (15:85) followed by ethyl acetate/hexane (60:40). Fractions of the product were combined and concentrated to give a colorless liquid (0.94 g). Mass spectral analysis of the product gave MH+=318.1135 [expected mass for $C_{12}H_{17}F_5NO_3$ (MH+)=318.1129].

IC. Synthesis of 2-(2,2,3,3,3-pentafluoro-1-oxopropyl) pyrrolidine hydrochloride (Scheme I, compound Vb)

Into a stirred solution of 2-(2-(2,2,3,3,3-pentafluoro-1-oxopropyl)-1-pyrrolidinecarboxylic acid, 1,1-dimethylethyl ester (compound from Example IB; 121 mg, 0.38 mmol) in ethyl acetate (15 ml), cooled to 0° C. in an ice-water bath, was bubbled HCl gas for 5 minutes. The bubbling of HCl was ceased and the reaction was capped and stirred for an additional 2 hours. The reaction was then concentrated to a colorless oil and dried under high vacuum over KOH pellets for 3 hours producing a solidified product (103 mg).

Mass spectral analysis of the product gave MH+= 218.0601 [expected mass for $C_7H_9F_5NO$(MH+)=218.0604].

ID. Synthesis of 2-[[2-(2,2,3,3,3-pentafluoro-1-oxopropyl)-1-pyrrolidinyl]carbonyl]-1-pyrrolidinecarboxylic acid, phenylmethyl ester (Scheme I, compound VIIb)

To a stirred solution of CBZ-L-Pro-OH (0.62 g, 2.49 mmol) and a drop of DMF in methylene chloride (10 ml) under argon was added oxalyl chloride (0.26 ml; 2.99 mmol) which resulted in a vigorous evolution of gas. After the evolution of gas ceased, the reaction was stirred for an additional 30 minutes. The reaction was then concentrated to give, as a light yellow oil, N-carbobenzoxy-L-prolyl chloride (CBZ-L-Pro-Cl).

Methylene chloride (10 ml) was added to CBZ-L-Pro-Cl which was then reacted under argon with a suspension of 2-(2,2,3,3,3-pentafluoro-1-oxopropyl)pyrrolidine hydrochloride (compound from Example IC; 2.49 mmol) and N-methylmorpholine (0.54 ml; 4.98 mmol) dissolved in methylene chloride (7 ml). After 2.5 hours the reaction was concentrated and brought up in methylene chloride (1 ml) and the product purified by flash chromatography on silica gel column eluting with ethyl acetate/hexane (50:50). Product fractions were collected and concentrated to give the desired product (0.52 g) as a colorless oil.

Mass spectral analysis of the product gave MH+= 449.1508 [expected mass for $C_{20}H_{22}F_5N_2O_4$ (MH+)= 449.1500].

II. 4-[[2-(2,2,3,3,3-pentafluoro-1-oxopropyl)-1-pyrrolidinyl]carbonyl]-3-thiazolidinecarboxylic acid, phenylmethyl ester (Scheme I, compound VIIa)

IIA. Thiazolidine-3,4-dicarboxylic acid, 3-phenylmethyl ester (Scheme I, compound VIa)

To a vigorously stirred solution of L-thiazolidine-4-carboxylic acid (13.32 g, 0.10 mole) cooled in an ice-water bath was added benzyl chloroformate (15.70 ml, 0.11 mmol) and 2N sodium hydroxide (55 ml), alternating additions in 5 ml portions over 20 minutes. Ten minutes after the additions, the reaction was brought to room temperature and stirred for an additional 30 minutes. The reaction was then extracted with ethyl ether (3×75 ml) and the aqueous layer acidified with 6N HCl (approx. 20 ml). The separated organics were collected and dissolved in ethyl ether (100 ml) and washed with brine (50 ml). The organic phase was dried over sodium sulfate and then concentrated to a viscous colorless oil (20.4 g).

IIB. Synthesis of 4-[[2-(2,2,3,3,3-pentafluoro-1-oxopropyl)-1-pyrrolidinyl]carbonyl]-3-thiazolidinecarboxylic acid, phenylmethyl ester (Scheme I, compound VIIa)

To a stirred solution of CBZ-L-ThioPro-OH (compound from Example IIa; 267 mg; 1.00 mmol) and NMM (0.12 ml; 1.05 mmol) in methylene chloride (15 ml) under argon and cooled to −17° C. was added isobutyl chloroformate (0.13 ml; 1.00 mmol). After 20 minutes, additional NMM (0.12 ml; 1.05 mmol) was added followed by a light suspension of 2-(2,2,3,3,3-pentafluoro-1-oxopropyl)pyrrolidine hydrochloride (compound IC; 253 mg; 1.00 mmol) in acetonitrile (10 ml) over a period of several minutes. After 1½ hours at −20° C. the reaction was allowed to warm to room temperature and stirred for an hour. The reaction was then concentrated and methylene chloride (3 ml) was added to the residue which was loaded onto a 4×15 cm silica gel column. The column was eluted with 400 ml of ethyl acetate/hexane (30:70) followed by ethyl acetate/hexane (35:65). Fractions containing the product were combined and concentrated to give a colorless viscous oil (63 mg). [1]Mass spectral analysis of the product gave MH+=467.1053 [expected mass for $C_{19}H_{20}F_5N_2O_4S$ (MH+)=467.1064].

III. Synthesis of 4-[[4-[(methoxymethylamino)carbonyl]-3-thiazolidinyl]carbonyl]-3-thiazolidinecarboxylic acid, 1,1-dimethylethyl ester (Scheme I, compound VIII)

IIIA. Synthesis of thiazolidine-3,4-dicarboyxlic acid, 3-(1,1-dimethylethyl)ester, (Scheme I, Compound Ia).

To a vigorously stirred suspension of L-thiazolidine-4-carboxylic acid (10.0 g; 75.09 mmol) in THF/H2O (1:1; 100 ml) was added sodium carbonate (11.94 g; 0.11 mole) followed by di-tert-butyl dicarbonate (16.39 g; 75.09 mmol). The resultant suspension was stirred overnight at room temperature. The reaction was then filtered, the filtrate transferred to a separatory funnel containing diethyl ether (100 ml) and the layers separated. The aqueous layer was covered with fresh diethyl ether (200 ml) and acidified with 1N aqueous hydrochloric acid. The organic layer was then washed with 0.5N aqueous hydrochloric acid followed by brine (50 ml), dried over magnesium sulfate and concentrated to give a white solid (14.56 g). $^1$H-NMR spectra was consistent with the expected structure: 10.56(s-1H, $CO_2H$), 4.78 (m-1H, CH), 4.59 and 4.39 (pr d, 2H, J=8 Hz; $NCH_2S$), 3.22–3.36 (m, 2H, $CH_2S$), 1.43 [s, 9H, $OC(CH_3)_3$].

IIIB. Synthesis of 4-[(methoxymethylamino)carbonyl]-3-thiazolidinecarboxylic acid, 1,1-dimethylethyl ester (Scheme I, compound IIa)

To a stirred solution of thiazolidine-3,4-dicarboxylic acid, 3-(1,1-dimethylethyl) ester (2.33 g; 9.99 mmol) and DMAP (1.22 g; 9.99 mmol) in methylene chloride (40 ml) under argon was added a suspension of N,O-dimethylhydroxyamine hydrochloride (0.98 g; 9.99 mmol) and NMM (1.10 ml; 9.99 mmol) in methylene chloride (15 ml). Water soluble carbodiimide (1.92 g, 9.99 mmmol) was then added to the solution and the reaction was allowed to proceed overnight. The reaction was then concentrated to about 15 ml and purified by flash chromatography by loading the suspension onto a 6×10 cm silica gel column and eluting with ethyl acetate/hexane (50:50). Fractions containing the product (Rf=0.39) were combined and concentrated to give a colorless oil (1.95 g). Mass spectral analysis of the product gave MH+=277.1216 [expected mass for $C_{11}H_{21}N_2O_4S$ (MH+)=277.1222].

IIIC. Synthesis of N-methoxy-N-methyl-4-thiazolidinecarboxamide, monohydrochloride, (Scheme I, compound Into a stirred solution of 4-[(methoxymethylamino)carbonyl]-3-thiazolidinecarboxylic acid, 1,1-dimethylethyl ester (compound from Example IIIB; 1.05 g, 3.80 mmol) in ethyl acetate cooled in an ice-$H_2O$ bath was bubbled HCl gas for 10 minutes. After addition of the gas, the reaction was capped and stirred for an additional 2 hours. The reaction was then concentrated to a colorless oil and dried under high vacuum over KOH pellets for 3 hours producing a solidified white solid (0.76 g).

IIID. Synthesis of 4-[[4-[(methoxymethylamino)carbonyl]-3-thiazolidinyl]carbonyl]-3-thiazolidine carboxylic acid, 1,1-dimethylethyl ester (Scheme I, compound VIII).

To a stirred solution of 3,4-thiazolidinedicarboxylic acid, 3-(1,1-dimethylethyl) ester (compound from Example IIIA; 0.81 g, 3.49 mmol) and DMAP (0.43 g, 3.49 mmol) in methylene chloride (20 ml) under argon was added NMM (0.38 ml, 3.49 mmol) followed by N-methoxy-N-methyl-4-thiazolidinecarboxamide, monohydrochloride (compound from Example IIIC; 0.76 g, 3.49 mmol) in methylene chloride (10 ml) and water soluble carbodiimide (0.67 g; 3.49 mmol). After the reaction was complete the reaction was concentrated to about 10 ml and loaded onto a 5×13 cm silica gel column and subjected to flash chromatography, eluting with acetone/ethyl acetate (8:92). Product containing fractions were combined (Rf=0.66) and concentrated to give a white foam (0.35 g). Mass spectral analysis of the product gave MH+=392.1324 [expected mass for $C_{15}H_{60}N_3O_5S_2$ (MH+)=392.1314].

IV. Synthesis of 4-[[4-(2,2,3,3,3-pentafluoro-1-oxopropyl)-3-thiazolidinyl]carbonyl]-3-thiazolidinecarboxylic acid, 1,1-dimethylethyl ester (Scheme I, compound IX)

IVA. Synthesis of 4-[[4-(2,2,3,3,3-pentafluoro-1-oxopropyl)-3-thiazolidinyl]carbonyl]-3-thiazolidinecarboxylic acid, 1,1-dimethylethyl ester (Scheme I, compound IX)

To a stirred solution of 4-[[4-[(methoxymethylamino)carbonyl]-3-thiazolidinyl]carbonyl]-3-thiazolidine carboxylic acid, 1,1-dimethylethyl ester (compound from Example IIID; 0.33 g, 0.84 mmol) in ethyl ether (30 ml) under argon at −78° C. was added perfluoroethyl iodide (0.32 ml, 2.70 mmol) followed by methyl lithium.lithium bromide (1.57 ml, 2.36 mmol, 1.5M in ethyl ether). TLC indicated the reaction was complete. The reaction was poured into 100 ml ethyl ether containing 25 g silica gel. Residual amounts of product in the flask were dissolved in ethyl ether and added to the silica/ether solution. Subsequently, the organic phase was removed and the silica gel was washed with ethyl ether (2×100 ml). The combined organics were dried over magnesium and sodium sulfate and then filtered and evaporated to give an oily white foam (0.34 g). The material was then flash chromatographed on a 4×10 cm silica gel column eluting with 0.4 liter of ethyl acetate/hexane (30:70) followed by 0.5 liter of ethyl acetate/hexane (75:25). Product containing fractions were combined and concentrated to an oil (49 mg).

Mass spectral analysis of the product gave (MH+)= 451.0799 (expected mass for $C_{15}H_{20}F_5N_2O_4S_2$ (MH+)= 451.0785).

Synthetic Assays

Synthetic reactions were generally followed by TLC on Analtech silica gel plates developed in ethyl acetate:hexane solvents. Compounds were identified by treating the plate with alkaline potassium permanganate followed by heating.

V. Enzyme Inhibition Assays

Prolyl endopeptidase was partially purified from bovine brain essentially as described by Yoshimoto et al. (Biochem., 94, 1179 (1983)) except that 50 mM HEPES, pH 7.4, was used instead of Tris buffer. This enzyme preparation is suitable for routine inhibition measurements; however, the enzyme may be further purified as described below. The state of purity of the enzyme is not expected to effect the measured $K_i$. The pellet from the 50%–80% ammonium sulfate cut is redissolved in the homogenization buffer and desalted by passage through a Pharmacia Mono Q column (0.5×5 cm) at 1 ml/min and the column is washed with 5 ml of buffer A to buffer B (total 20 ml; buffer A=50 mM HEPES, pH 7.4, 1 mM EDTA and 1 mM DTT; buffer B=buffer A+0.5M NaCl). Enzyme activity elutes at about [NaCl]=0.25M. Preliminary data suggest that the enzyme is not stable in storage for long periods (over 1 to 2 months) and therefore fresh preparations of the enzyme are preferred.

The enzyme is assayed in buffer A (3.0 ml) at 37° C. containing 20 µM substrate (CBz-Gly-Pro-p-nitroanilide). The increase in absorbance at 410 nm is monitored (410 nm =8.4 $mM^{-1}cm^{-1}$). Inhibitor stock solutions are made in DMSO. To characterize reversible competitive inhibitors, the initial rates in the presence of three inhibitor concentrations are measured using [S]=50 µM ($K_M$ for the substrate is 11 µM). If slow binding is observed, the final equilibrium rates are used.

The $K_i$ for a competitive inhibitor is calculated using known formulas: $v_o/v_i=(1+[I]/K_i$, app) and $K_i=K_i$, app/(1+ $[S]/K_M$), where $v_o$ is the initial rate in the absence of inhibitor, $v_i$ is the initial rate in the presence of inhibitor at the concentration [I], and [S] is the substrate concentration. If "slow binding" is observed (i.e. if the approach to the binding equilibrium is slow), the final steady-state rate rather than the initial rate is taken as $v_i$.

Enzyme inhibition constants were found using the described methods for various compounds of formula 1. Table 2 represents the data found for the tested compounds indicated.

TABLE 2

| COMPOUNDS | MDL NO. | ENZYME INHIBITION |
|---|---|---|
| 2-[[2-(2,2,3,3,3-pentafluoro-1-oxopropyl)-1-pyrrolidinyl]carbonyl]-1-pyrrolidinecarboxylic acid, phenylmethyl ester | EXAMPLE I 100,527-01 | $1.4 \times 10^{-9}$ M |
| 4-[[2-(2,2,3,3,3-pentafluoro-1-oxopropyl)-1-pyrrolidinyl]carbonyl]-3-thiazolidinecarboxylic acid, phenylmethyl ester | EXAMPLE II 102,916-01 | $1.0 \times 10^{-9}$ M |
| 4-[[4-(2,2,3,3,3-pentafluoro-1-oxopropyl)-3-thiazolidinyl]carbonyl-3-thiazolidinecarboxylic acid, 1,1-dimethylethyl ester | EXAMPLE IV 100,676-01 | $1.0 \times 10^{-9}$ M |

Compounds may also be tested in vivo for inhibition in a variety of ways, including such as those described by Atack (Atack, Eur. J. Pharm., 205, 157–163 (1991) or by other methods described and known in the art. For instance compounds may be injected in saline or with a carrier such as methyl celluose i.p. into male BKTO mice (25–30 g) and at appropriate times sacrificed and the brains and kidneys removed. Organs can be homogenized in 10 ml (about 20 volumes) of ice-cold assay buffer. Aliquots of the homogenates can then be used to determine protein concentration such as by the method of Lowry, et. al (Lowry, et al., J. Biol. Chem. 193, 265 (1951). Dissociation of the inhibitor can be minimized by using 199 ul aliquots of the crude homogenate using a 2 minute incubation at room temperature, with the total time between sacrifice of the animal and termination of the assay being around 3 minutes. Activity may be expressed as activity per mg of protein and express as a percent relative to vehicle-treated animals.

Behavioral effects on memory by compounds can be tested in a variety of ways, including those described by Atack (Atack, Eur. J. Pharm., 205, 157–163 (1991). Effects of compounds on memory may be tested by measuring reversal of scopolamine-induced memory deficits in a mouse passive-avoidance model. In such a model mice are assigned to various groups which receive injections of either (1) vehicle; (2) vehicle and scoploamine (i.e., ~0.2 mg/Kg); or (3) various dosages of compound (i.e., ~0.1 mg/Kg–1.0 mg/Kg). Mice are then placed in an illuminated side of a two chamber, light/dark box. On entering the dark side of the box, the animal receives a short electric shock (i.e. ~2 seconds, ~0.4 mA). The time taken to enter the dark chamber (the step-through latency) is recorded. The following day, the mice are returned to the light side of the box and the time taken to step-through to the dark side is recorded. Memory deficits in this model are directly related to the differences in the time taken to step-through to the dark side in the two consecutive days. A longer step-through time on the second day would be a display of memory, whereas no difference in step-through time would indicate a memory deficit.

Changes and modifications in the specifically described embodiments can be carried out without departing from the scope of the invention which is intended to be limited only by the scope of the appended claims.

What is claimed is:

1. A compound of formula 1, including all of its stereoisomers:

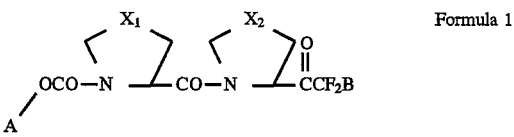

Formula 1 wherein;

A is benzyl or a t-butyl protecting group;

X1 is —S—;

X2 is —S—; and

B is $CF_3$ or $CF_2CF_3$.

2. A compound of claim 1 wherein the compound is 4-[[2-(2,2,3,3,3-pentafluoro-1-oxypropyl)-3-thiazolidinyl] carbonyl-3-thiazolidinecarboxylic acid, 1,1-dimethyl ester.

3. A pharmaceutical composition comprising a compound of according to claims 1 or 2 and a pharmaceutically acceptable carrier.

4. A method of memory enhancement in a patient in need thereof comprising administering an effective amount of a compound or pharmaceutical composition of according to claims 1 or 2.

5. A method of preventing or slowing the affects of amnesia in a patient in need thereof comprising administering an effective amount of a compound or pharmaceutical composition of according to claims 1 or 2.

6. A method of preventing or slowing memory deficits in a patient in need thereof comprising administering an effective amount of a compound or pharmaceutical composition of according to claims 1 or 2.

* * * * *